(12) United States Patent
Chandanson et al.

(10) Patent No.: US 9,833,263 B2
(45) Date of Patent: Dec. 5, 2017

(54) BONE ANCHOR ASSEMBLIES WITH ORIENTATION INDICATOR

(71) Applicant: Medos International Sarl, Le Locle (CH)

(72) Inventors: Thibault Chandanson, Villers le lac (FR); Frank Spratt, Middleboro, MA (US); Ernest Quintanilha, Norton, MA (US); Philip Cormier, Canton, MA (US)

(73) Assignee: Medos International Sarl, Le Locle (CH)

( * ) Notice: Subject to any disclaimer, the term of this patent is extended or adjusted under 35 U.S.C. 154(b) by 117 days.

(21) Appl. No.: 14/685,431

(22) Filed: Apr. 13, 2015

(65) Prior Publication Data

US 2016/0296256 A1 Oct. 13, 2016

(51) Int. Cl.
*A61B 17/70* (2006.01)
*A61B 17/88* (2006.01)
(Continued)

(52) U.S. Cl.
CPC ...... *A61B 17/7037* (2013.01); *A61B 17/7032* (2013.01); *A61B 17/8605* (2013.01); *A61B 2017/00115* (2013.01)

(58) Field of Classification Search
CPC ............ A61B 17/7037; A61B 17/7032; A61B 17/8605
(Continued)

(56) References Cited

U.S. PATENT DOCUMENTS 5,672,176 A * 9/1997 Biedermann ...... A61B 17/7037
606/271
6,471,705 B1 * 10/2002 Biedermann ...... A61B 17/7032
606/271
(Continued)

FOREIGN PATENT DOCUMENTS

EP 2052690 A1 4/2009
EP 2468198 A1 6/2012
(Continued)

OTHER PUBLICATIONS

Invitation to Pay Additional Fees/Partial International Search for Application No. PCT/US2016/027064, dated Jul. 8, 2016 (7 pages).
(Continued)

*Primary Examiner* — Pedro Philogene
*Assistant Examiner* — David C Comstock
(74) *Attorney, Agent, or Firm* — Nutter McClennen & Fish LLP (57) ABSTRACT

Bone anchor assemblies are disclosed herein that include one or more features for indicating the relative positioning of the receiver member and the shank, or for selectively maintaining the receiver member and the shank in a fixed relative position. For example, the head of the shank can include a surface feature that interacts with a drag ring to provide tactile or audible feedback when the shank is positioned at a particular orientation with respect to the receiver member. By way of further example, the head of the shank and a compression cap disposed in the receiver member can each include engagement features that cooperate to allow for selective locking of the orientation of the shank with respect to the receiver member.

17 Claims, 6 Drawing Sheets

(51) Int. Cl.
*A61B 17/86* (2006.01)
*A61B 17/00* (2006.01)

(58) Field of Classification Search
USPC .................................................. 606/266–272
See application file for complete search history.

(56) References Cited

U.S. PATENT DOCUMENTS

| | | | |
|---|---|---|---|
| 7,722,652 B2 * | 5/2010 | Justis | A61B 17/7035 606/267 |
| 7,922,748 B2 * | 4/2011 | Hoffman | A61B 17/7037 606/264 |
| 2006/0200131 A1 | 9/2006 | Chao et al. | |
| 2011/0160778 A1 | 6/2011 | Elsbury | |
| 2013/0096618 A1 | 4/2013 | Chandanson et al. | |
| 2014/0094849 A1 | 4/2014 | Spratt et al. | |
| 2014/0094862 A1 | 4/2014 | Cormier et al. | |
| 2014/0257411 A1 | 9/2014 | Rezach | |
| 2014/0277137 A1 | 9/2014 | Stad et al. | |
| 2014/0277153 A1 | 9/2014 | Spratt et al. | |
| 2014/0277157 A1 | 9/2014 | Chandanson et al. | |
| 2014/0277158 A1 | 9/2014 | Spratt et al. | |
| 2014/0277159 A1 | 9/2014 | Spratt et al. | |
| 2014/0277161 A1 | 9/2014 | Spratt et al. | |
| 2014/0277189 A1 | 9/2014 | Spratt et al. | |
| 2014/0277198 A1 | 9/2014 | Stad | |
| 2016/0166304 A1 | 6/2016 | Stad et al. | |

FOREIGN PATENT DOCUMENTS

| | | |
|---|---|---|
| FR | 2993170 A1 | 1/2014 |
| WO | 2012/091737 A1 | 7/2012 |
| WO | 2015/029042 A1 | 3/2015 |

OTHER PUBLICATIONS

International Search Report and Written Opinion for Application No. PCT/US2016/027064, dated Sep. 28, 2016 (8 pages).

* cited by examiner

BONE ANCHOR ASSEMBLIES WITH ORIENTATION INDICATOR

FIELD

Bone anchor assemblies with features for indicating orientation are disclosed herein, as are methods related thereto.

BACKGROUND

Bone anchor assemblies can be used in orthopedic surgery to fix bone during healing, fusion, deformity correction, or other processes. In spinal surgery, for example, bone anchor assemblies can be used to secure a spinal fixation element to one or more vertebrae to rigidly or dynamically stabilize the spine.

Bone anchor assemblies traditionally include an elongate shank with a proximal head and a receiver member in which the proximal head of the shank is received. The receiver member can also receive a spinal stabilization element therein, such as a spinal rod. The receiver member can be configured to allow for various types of motion of the shank with respect thereto (e.g., polyaxial motion, uniplanar motion, favored angle motion, etc.).

The capacity for the shank to angulate with respect to the receiver member can make it difficult to visually assess the orientation or trajectory of the shank, for example when the shank is at least partially advanced into bone or during minimally-invasive procedures in which visibility of the shank is limited. In addition, while motion between the receiver member and the shank can be desirable during some portions of a surgical procedure, it can be undesirable during other portions (e.g., during derotation maneuvers or during insertion of the bone anchor assembly).

SUMMARY

Bone anchor assemblies are disclosed herein that include one or more features for indicating the relative positioning of the receiver member and the shank, or for selectively maintaining the receiver member and the shank in a fixed relative position. For example, the head of the shank can include a surface feature that interacts with a drag ring to provide tactile or audible feedback when the shank is positioned at a particular orientation with respect to the receiver member. By way of further example, the head of the shank and a compression cap disposed in the receiver member can each include engagement features that cooperate to allow for selective locking of the orientation of the shank with respect to the receiver member.

In some embodiments, a bone anchor assembly includes a bone anchor having a proximal head and a distal shank; and a receiver member having a seat formed therein configured to movably seat the head of the bone anchor such that the shank of the bone anchor can be positioned at a plurality of angles with respect to the receiver member. The head of the bone anchor includes an orientation indication feature that engages an orientation indication feature of the receiver member to provide feedback when the shank is positioned in a predetermined orientation with respect to the receiver member.

The indication feature of the head can include a groove formed in the head and the indication feature of the receiver member can include a drag ring configured to engage the groove when the shank is positioned in the predetermined orientation. The groove can extend circumferentially around the head, perpendicular to a longitudinal axis of the bone anchor. In some embodiments, the drag ring is seated within the groove only when the bone anchor is positioned at the predetermined orientation with respect to the receiver member. The indication feature of the head can include first and second radial protrusions formed on the head and the indication feature of the receiver member can include a drag ring configured to sit between the first and second radial protrusions when the shank is positioned in the predetermined orientation. The first and second radial protrusions can extend circumferentially around the head, perpendicular to a longitudinal axis of the bone anchor. The indication feature of the receiver member can include a groove formed in the seat of the receiver member and the indication feature of the head can include a drag ring configured to engage the groove when the shank is positioned in the predetermined orientation. The indication feature of the receiver member can include first and second radial protrusions formed on the seat of the receiver member and the indication feature of the head can include a drag ring configured to sit between the first and second radial protrusions when the shank is positioned in the predetermined orientation. The predetermined orientation can be one in which a longitudinal axis of the bone anchor is parallel to a longitudinal axis of the receiver member. The predetermined orientation can be one in which the bone anchor is positioned at a maximum angle with respect to the receiver member. The predetermined orientation can be one in which the bone anchor is positioned normal to an obliquely-angled distal-facing surface of the receiver member. The head can include a plurality of orientation indication features, each of the plurality of orientation indication features being configured to engage an orientation indication feature of the receiver member to provide feedback when the shank is positioned in a corresponding one of a plurality of predetermined orientations with respect to the receiver member.

In some embodiments, a bone anchor assembly includes a bone anchor having a proximal head and a distal shank, the proximal head including a planar surface and a spherical surface, a receiver member having a polyaxial seat formed in a distal end thereof and configured to polyaxially seat the head of the bone anchor, and a compression member disposed within the receiver member and having a distal end that engages the proximal head of the bone anchor, the distal end including a planar surface. The assembly can be positionable in a first locked configuration in which the planar surface of the head and the planar surface of the compression member are parallel to and engaged with one another to lock an orientation of the shank relative to the receiver member. The assembly can be positionable in a second locked configuration in which the planar surface of the head and the planar surface of the compression member are not parallel to one another and in which the compression member engages the head to lock an orientation of the shank relative to the receiver member. The planar surface of the head can include a proximal-facing terminal end surface of the bone anchor. The planar surface of the head can include a proximal-facing surface of a groove formed in the head at a location distal to a proximal-most end of the bone anchor. The planar surface of the compression member can include a distal-facing surface of an annular ridge formed on the compression member. The assembly can be biased towards the first locked configuration.

In some embodiments, a surgical method includes advancing a distal shank of a bone anchor into a bone while a proximal head of the bone anchor is seated in a receiver member; adjusting an angle of the receiver member with respect to the bone anchor until an orientation indication feature of the head engages an orientation indication feature of the receiver member to generate feedback indicative of a relative positioning between the bone anchor and the receiver member; and determining a trajectory of the bone anchor in the bone based on the relative positioning indicated by said feedback.

The method can include positioning a planar surface of a compression member disposed in the receiver member with respect to a planar surface of the head such that the planar surfaces are parallel to and engaged with one another to lock a relative position between the bone anchor and the receiver member.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Bone anchor assemblies are disclosed herein that include one or more features for indicating the relative positioning of the receiver member and the shank, or for selectively maintaining the receiver member and the shank in a fixed relative position. For example, the head of the shank can include a surface feature that interacts with a drag ring to provide tactile or audible feedback when the shank is positioned at a particular orientation with respect to the receiver member. By way of further example, the head of the shank and a compression cap disposed in the receiver member can each include engagement features that cooperate to allow for selective locking of the orientation of the shank with respect to the receiver member.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the present disclosure, like-numbered components of the embodiments generally have similar features and/or purposes. Further, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the size and shape of the components with which the systems and devices are being used, the anatomy of the patient, and the methods and procedures in which the systems and devices will be used. The figures provided herein are not necessarily to scale.

Figure 1:
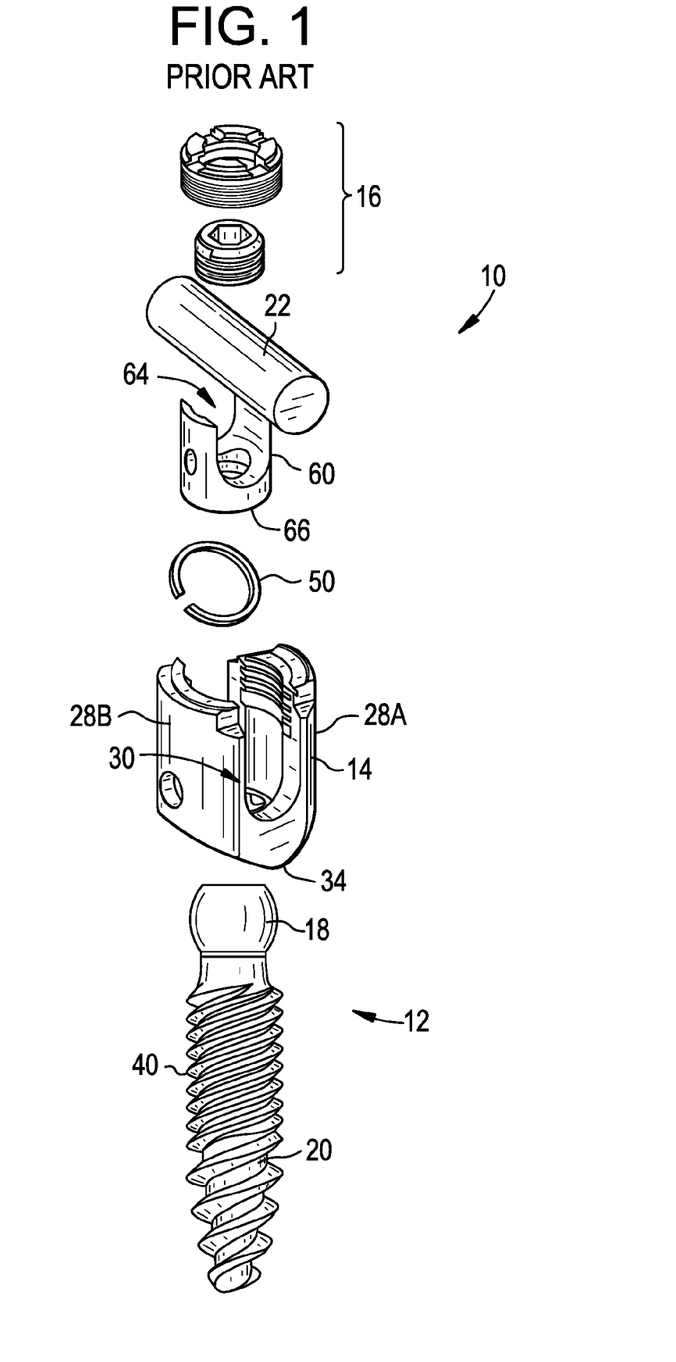
FIG. 1 is a perspective view of a prior art bone anchor assembly.

FIG. 1 illustrates a prior art bone anchor assembly 10 that includes a bone anchor 12, a receiver member 14 for receiving a spinal fixation element, such as a spinal rod 22, to be coupled to the bone anchor 12, and a closure mechanism 16 to capture the spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end having a pair of spaced apart arms 28A, 28B defining a recess 30 therebetween and a distal end having a distal end surface 34 defining an opening through which at least a portion of the bone anchor 12 extends. The closure mechanism 16, e.g., dual inside set screws as shown, can be positionable between and can engage the arms 28A, 28B to capture the spinal fixation element 22 within the receiver member 14 and fix the spinal fixation element with respect to the receiver member.

The proximal head 18 of the bone anchor 12 is generally in the shape of a truncated sphere having a planar proximal surface and an approximately spherically-shaped distal surface. The illustrated bone anchor assembly is a polyaxial bone screw designed for posterior implantation in the pedicle or lateral mass of a vertebra. The proximal head 18 of the bone anchor 12 engages a distal end of the receiver member 14 in a ball and socket like arrangement in which the proximal head 18 and the distal shaft 20 can pivot relative to the receiver member 14. The distal shaft 20 of the bone anchor 12 can be configured to engage bone and, in the illustrated embodiment, includes an external bone engaging thread 40. The bone anchor 12 can be selectively fixed relative to the receiver member 14. Prior to fixation, the bone anchor 12 is movable relative to the receiver member 14 within a cone of angulation generally defined by the geometry of the distal end of the receiver member and the proximal head 18 of the bone anchor 12.

A drag ring 50 can be disposed between the head 18 of the bone anchor 12 and the receiver member 14 to provide frictional engagement therebetween. The drag ring 50 can have a variety of configurations, shapes, and sizes, and generally can be configured to expand to fit around at least a portion of the head 18 of the bone anchor 12 and to thereby exert a frictional drag force on the head 18. The illustrated drag ring 50 is a generally C-shaped loop with an opening formed therein that allows a diameter of the ring to expand to fit around a portion of the spherical head 18 of the bone anchor 12. The expanded ring 50 can be seated within a retaining groove (not shown) formed within the recess 30 of the receiver member 14.

The compression member 60 can be positioned within the receiver member 14 and interposed between the spinal fixation element 22 and the proximal head 18 of the bone anchor 12 to compress a distal outer surface of the proximal head 18 into direct, fixed engagement with the distal inner surface of the receiver member 14. The compression member 60 can include a pair of spaced apart arms that define a U-shaped seat 64 for receiving the spinal fixation element 22 and a spherical distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread provided on the arms 28A, 28B of the receiver member 14. In other embodiments, however, the closure mechanism 16 can include an outer set screw operable to act on the compression member 60 and an inner set screw operable to act on the rod 22. The receiver member 14 can include or can be coupled to one or more extension tabs (not shown) that extend proximally from the receiver member 14 to functionally extend the length of the arms 28A, 28B. The extension tabs can facilitate installation and assembly of a fixation or stabilization construct and can be removed prior to completing a surgical procedure.

In use, bone can be prepared to receive the bone anchor assembly 10, generally by tapping a hole in the bone which is sized appropriately to receive the bone anchor 12. If not already completed, the bone anchor assembly 10 can be assembled, which can include assembling the bone anchor 12 and the receiver member 14, so that the distal shaft 20 extends through the opening in the distal end of the receiver member 14 and the proximal head 18 of the bone anchor 12 is received in the distal end of the receiver member 14. Once the anchor 12 is inserted into the receiver member 14, a driver tool can be fitted with the bone anchor 12 to drive the bone anchor 12 into the prepared hole in the bone. The compression member 60 can be positioned within the receiver member 14 such that the arms of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. A torsional force can be applied to the closure mechanism 16 to move it within the recess 30 so as to force the spinal rod 22 into engagement with the compression member 60 and to in turn force the compression member 60 onto the proximal head 18 of the bone anchor 12, thereby fixing the spinal rod 22 relative to the receiver member 14 and locking the angular position of the bone anchor 12 relative to the receiver member 14.

One or more embodiments of inventive bone anchor assemblies are described below. Except as indicated below and as will be readily apparent to one having ordinary skill in the art, the structure, operation, and use of these embodiments is similar or identical to that of the bone anchor assembly 10 described above. Accordingly, a detailed description of said structure, operation, and use is omitted here for the sake of brevity. Bone anchor assemblies are sometimes referred to herein simply as "bone anchors."

Figure 2:
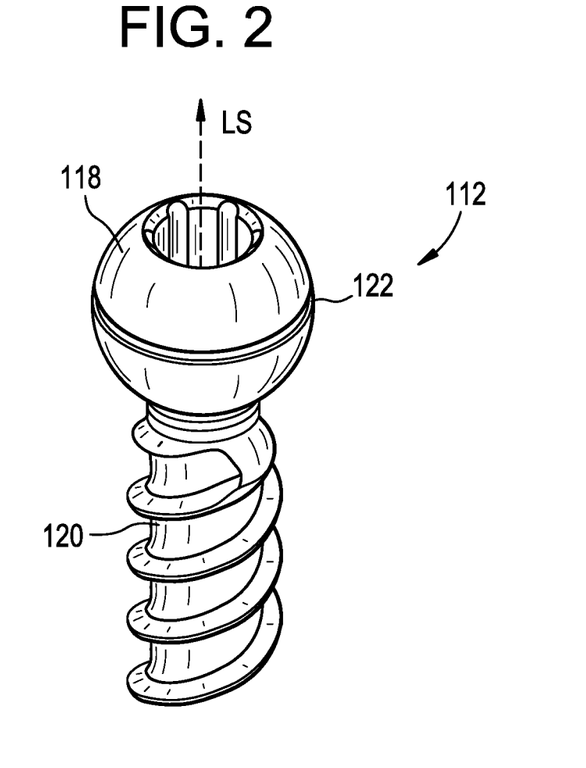
FIG. 2 is a perspective view of a bone anchor having an orientation indication feature.
Figure 3:
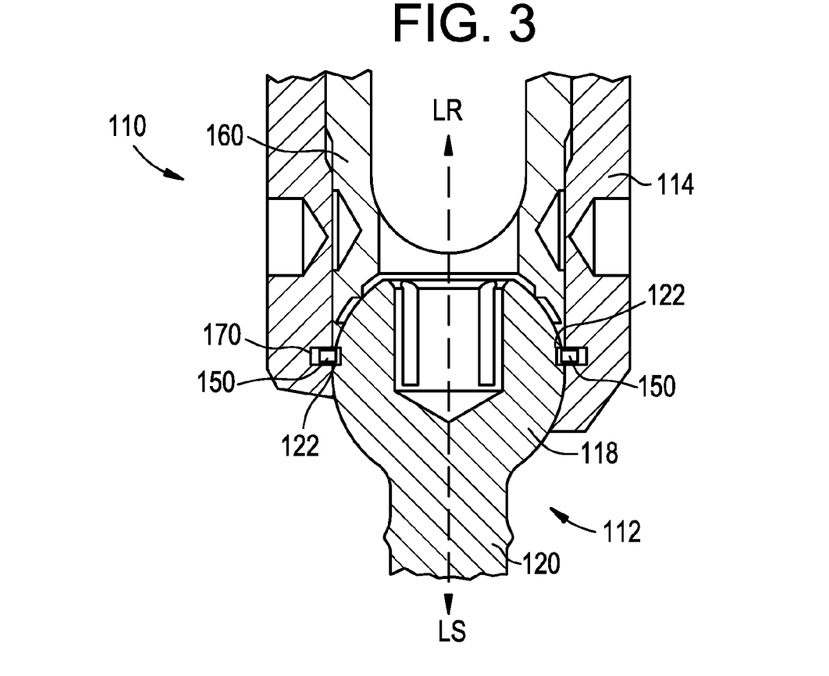
FIG. 3 is a sectional view of a bone anchor assembly including the bone anchor of FIG. 2.
Figure 4:
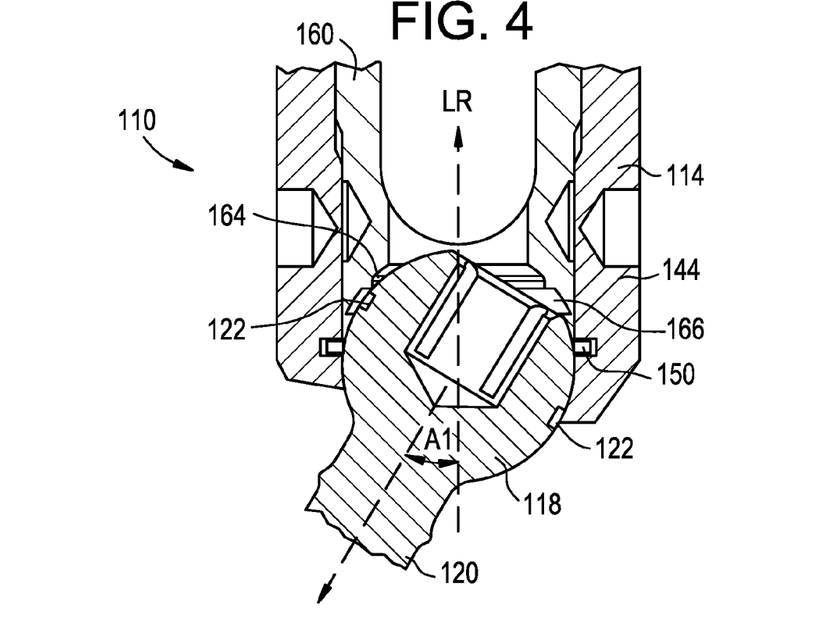
FIG. 4 is another sectional view of the bone anchor assembly of FIG. 3.

FIGS. 2-4 illustrate an exemplary embodiment of a bone anchor 112 for use with a bone anchor assembly 110, similar to the bone anchor assembly 10 described above. The illustrated bone anchor 112 includes a proximal head 118 and a distal, bone engaging shank 120. The head 118 has a ring-shaped recess or groove 122 formed therein that can function as an orientation indication feature for indicating an orientation of the shank 120 with respect to the receiver member 114 (e.g., when the shank itself is not visible to a user). In particular, an orientation indication feature of the receiver member 114, such as a drag ring 150, can engage the recess 122 to indicate that the shank 120 is positioned in a predetermined orientation with respect to the receiver member. When the ring 150 or other indication feature of the receiver member 114 engages or snaps into the recess 122, a mechanical resistance can be generated to maintain the relative alignment between the receiver member and the shank 120 and to provide tactile or audible feedback to a user that a particular alignment has been reached.

The recess 122 can extend entirely or partially about a circumference of the head 118. The recess 122 can be positioned at any of a variety of locations on the head 118, including just proximal of the equator of the head 118 (as shown), directly on the equator of the head, or at any other location. The recess 122 can also be formed at any of a variety of orientations. In the illustrated embodiment, the recess 122 extends perpendicular to a longitudinal axis LS of the shank 120. Since the drag ring 150 is disposed perpendicular to a longitudinal axis LR of the receiver member 114, the recess 122 and the ring 150 engage one another when the longitudinal axis LS of the shank 120 is aligned with the longitudinal axis LR of the receiver member 114. It will be appreciated that the recess 122 can be positioned at other angles with respect to the longitudinal axis LS (or the drag ring 150 and its corresponding groove 170 can be positioned at other angles with respect to the longitudinal axis LR) to indicate when other relative alignments have been reached. For example, the recess 122 and the ring 150 can be oriented such that feedback is provided when the shank 120 reaches a maximum angulation with respect to the receiver member 114, when the shank is disposed normal to an obliquely-angled distal-facing surface of the receiver member (e.g., in the case of a favored angle screw), or when the shank is at any other orientation of interest.

While a single recess 122 is shown, it will be appreciated that the head 118 can include a plurality of recesses. For example, the head 118 can include a plurality of recesses 122, each being disposed at a different angle with respect to the longitudinal axis LS of the shank 120, such that each recess provides an indication of a different relative positioning between the shank and the receiver member 114. The drag ring 150 can remain substantially stationary with respect to the receiver member 114, seated in the groove 170, when the bone anchor 112 is angulated with respect to the receiver member.

As shown in FIG. 3, when the shank 120 reaches a predetermined orientation with respect to the receiver member 114 (in the illustrated embodiment, one in which a longitudinal axis LS of the shank is parallel to the longitudinal axis LR of the receiver member), the drag ring 150 engages with the recess 122 to indicate that the predetermined orientation has been reached. In this predetermined orientation, at least a portion of the drag ring 150 can be seated in the groove 170 of the receiver member 114 and at least a portion of the drag ring can be seated in the recess 122 of the bone anchor 112.

As shown in FIG. 4, when the shank 120 is positioned with respect to the receiver member 114 in orientations other than the predetermined orientation (in the illustrated embodiment, such that the longitudinal axis LS of the shank is disposed at a non-zero angle A1 with respect to the longitudinal axis LR of the receiver member), the drag ring 150 does not engage the recess 122.

Other components of the receiver member 114 can also interact with the recess 122 to provide an indication of the relative positioning of the shank 120 and the receiver member. For example, the compression member 160 can include an annular ridge 164 formed on a distal-facing surface 166 thereof that is configured to engage the recess 122 (e.g., when the angle A1 reaches a predetermined maximum angle or some other desired angle).

The drag ring 150 or other component of the receiver member 114 can be configured to engage the recess 122 with any type of fit known in the art, such as a snap fit, a compression fit, an interference fit, etc. Engagement between the orientation indication features of the head 118 and the receiver member 114 can create a mechanical resistance that can be felt by a user to provide a tactile indication of the relative positioning between the bone anchor 112 and the receiver member. Alternatively, or in addition, this engagement can produce a sound that is audible to the user. The depth, shape, or other properties of the recess 122 can be selected such that the mechanical resistance is large enough to be felt by a user but small enough to be easily overcome to further angulate the construct if desired to move the shank 120 to another orientation.

In some embodiments, the orientation indicating features of the head 118 and the receiver member 114 can be reversed, yet achieve the same function. For example, the drag ring 150 can be mounted in a groove formed in the head 118 instead of a groove formed in the receiver member 114, and can be configured to remain stationary with respect to the head when the bone anchor 112 is angulated with respect to the receiver member. Similarly, the recess 122 can be formed in the seat of the receiver member 114, instead of in the head 118. In such embodiments, when the bone anchor 112 is moved to a position in which the drag ring 150 is aligned with the recess formed in the receiver member 114, the drag ring 150 can expand into the recess. This expansion can create a snapping or clicking noise and/or can be felt by a user as a slight increase in mechanical resistance against further angulation of the anchor 112, thus creating audible and/or tactile indicators that the shank 120 has reached a predetermined orientation.

It will be appreciated that any type and number of surface features can be formed on the head 118 or in the receiver member 114 to provide indications as to the orientation of a shank 120 of the bone anchor 112.

In use, the bone anchor assembly 110 can be implanted in a patient (e.g., in a bone structure such as a pedicle or lateral mass of a vertebra) using standard techniques. After the assembly is implanted, or at any time during the implantation of the assembly, the user can assess the trajectory of the shank 120 by adjusting the angle of the receiver member 114 with respect thereto until the orientation indicating features of the head 118 and the receiver member 114 engage one another. Such engagement can produce audible or tactile feedback to the user, or a resistance to further relative movement that is perceptible to the user, to indicate that a predetermined relative positioning of the shank 120 and the receiver member 114 has been reached. The user can know which predetermined relative positioning (coaxial, maximum angulation, etc.) is indicated by the feedback, said knowledge being obtained, for example, by inspecting the assembly before insertion or by reviewing training or packaging materials associated with the assembly. In the illustrated embodiment, the user can know that receipt of such feedback means that the longitudinal axis of the shank 120 is aligned with the longitudinal axis of the receiver member 114. The user can therefore estimate the trajectory of the shank 120 in bone by observing the angle of the receiver member 114 with respect to the bone (visually or otherwise) and estimating or extrapolating from that angle the angle of the shank 120 with respect to the bone. The user can also engage the indicator features of the head 118 and the receiver member 114 to temporarily or indefinitely maintain a predetermined angular position of the shank 120 with respect to the receiver member 114. This can be done after the assembly is implanted or at any time during implantation of the assembly.

Additional exemplary embodiments of bone anchors and bone anchor assemblies for providing an indication as to bone anchor orientation are described below. These bone anchors and bone anchor assemblies can generally be configured and used in a manner similar to those described above, with like-named and/or like-numbered elements having similar features.

Figure 5:
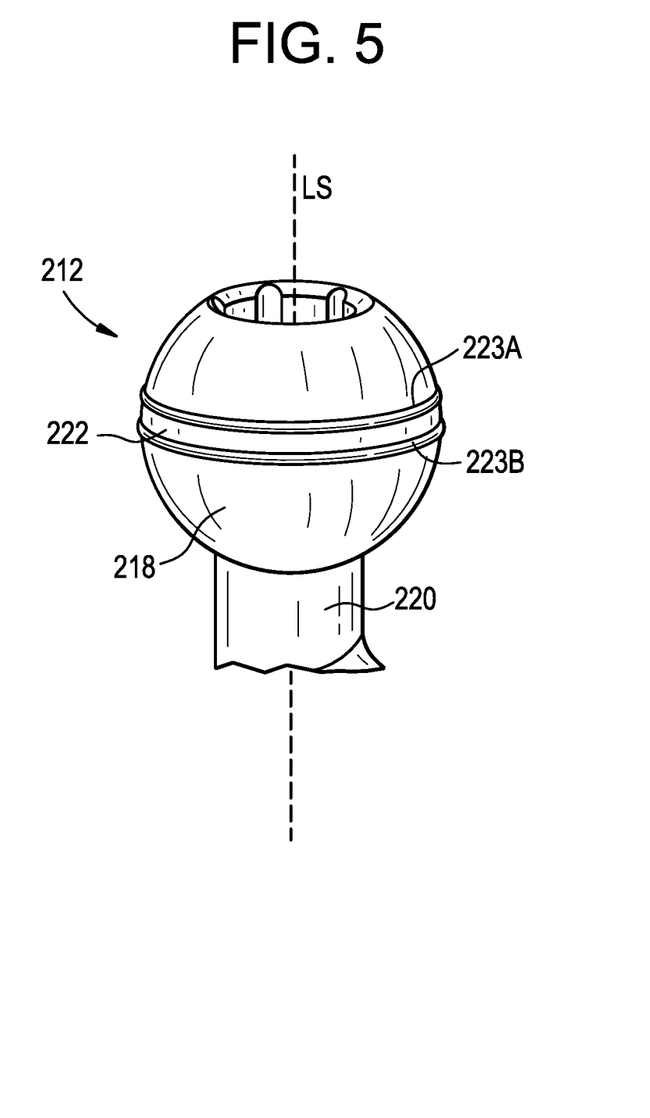
FIG. 5 is a perspective view of another embodiment of a bone anchor having an orientation indication feature.

FIG. 5 illustrates an exemplary bone anchor 212 that includes an orientation indication feature in the form of two spaced apart radial protrusions or ridges 223A, 223B that define a channel 222 therebetween. The ridges 223A, 223B can be included instead of or in addition to the recess 122 described above.

The drag ring 150 or other indication feature of the receiver member 114 can engage or snap into the channel 222 to generate a mechanical resistance to maintain the relative alignment between the receiver member and the shank 220 and to provide tactile or audible feedback to a user that a particular alignment has been reached.

The ridges 223A, 223B can extend entirely or partially about a circumference of the head 218. The ridges 223A, 223B can be positioned at any of a variety of locations on the head 218, including just proximal of the equator of the head 218 (as shown), directly on the equator of the head, or at any other location. The ridges 223A, 223B can also be formed at any of a variety of orientations. In the illustrated embodiment, the ridges 223A, 223B extend perpendicular to a longitudinal axis LS of the shank 220. Since the drag ring 150 is disposed perpendicular to a longitudinal axis LR of the receiver member 114, the ridges 223A, 223B and the ring 150 will engage one another when the longitudinal axis LS of the shank 220 is aligned with the longitudinal axis LR of the receiver member 114. It will be appreciated that the ridges 223A, 223B can be positioned at other angles with respect to the longitudinal axis LS (or the drag ring 150 and its corresponding groove 170 can be positioned at other angles with respect to the longitudinal axis LR) to indicate when other relative alignments have been reached. For example, the ridges 223A, 223B and the ring 150 can be oriented such that feedback is provided when the shank 220 reaches a maximum angulation with respect to the receiver member 114, when the shank is disposed normal to an obliquely angled distal-facing surface of the receiver member (e.g., in the case of a favored angle screw), or when the shank is at any other orientation of interest.

While a single pair of ridges 223A, 223B defining a single channel 222 is shown, it will be appreciated that the head 218 can include a plurality of ridges or pairs of ridges. For example, the head 218 can include a plurality of ridges or ridge pairs, each being disposed at a different angle with respect to the longitudinal axis LS of the shank 220, such that each ridge or ridge pair provides an indication of a different relative positioning between the shank and the receiver member 114.

The drag ring 150 or other component of the receiver member 114 can be configured to engage the channel 222 with any type of fit known in the art, such as a snap fit, a compression fit, an interference fit, etc. Engagement between the orientation indication features of the head 218 and the receiver member 114 can create a mechanical resistance that can be felt by a user to provide a tactile indication of the relative positioning between the bone anchor 212 and the receiver member. Alternatively, or in addition, this engagement can produce a sound that is audible to the user. The height, shape, or other properties of the ridges 223A, 223B can be selected such that the mechanical resistance is large enough to be felt by a user but small enough to be easily overcome to further angulate the construct if desired to move the shank 220 to another orientation.

In some embodiments, the orientation indicating features of the head 218 and the receiver member 114 can be reversed, yet achieve the same function. For example, the drag ring 150 can be mounted in a groove formed in the head 218 instead of a groove formed in the receiver member 114, and can be configured to remain stationary with respect to the head when the bone anchor 212 is angulated with respect to the receiver member. Similarly, the ridges 223A, 223B can be formed in the seat of the receiver member 114, instead of on the head 218. In such embodiments, when the bone anchor 212 is moved to a position in which the drag ring 150 is aligned with the channel 222 defined by the ridges 223A, 223B formed in the receiver member 114, the drag ring 150 can expand into the channel 222. This expansion can create a snapping or clicking noise and/or can be felt by a user as a slight increase in mechanical resistance against further angulation of the anchor 212, thus creating audible and/or tactile indicators that the shank 220 has reached a predetermined orientation.

The assembly 210 can be used in the same manner as the assembly 110 described above.

Figure 6:
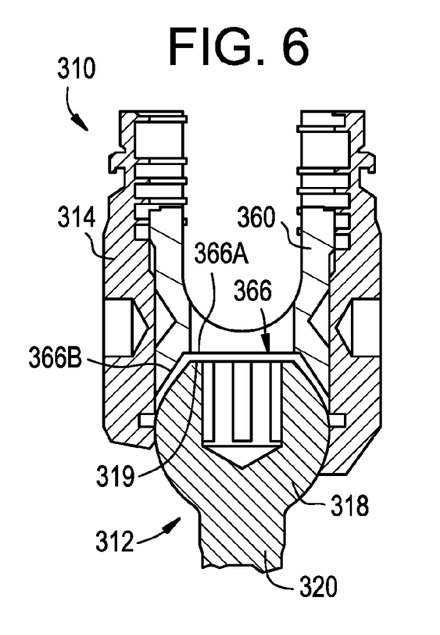
FIG. 6 is a sectional view of another embodiment of a bone anchor assembly having an orientation indication feature.
Figure 7:
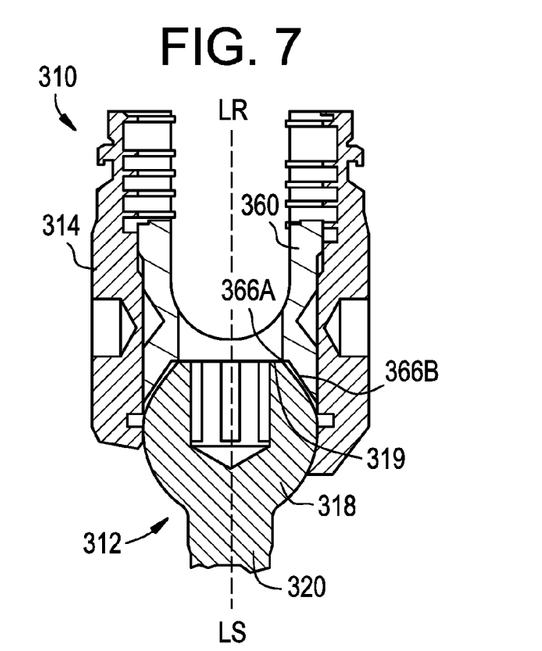
FIG. 7 is another sectional view of the bone anchor assembly of FIG. 6.
Figure 8:
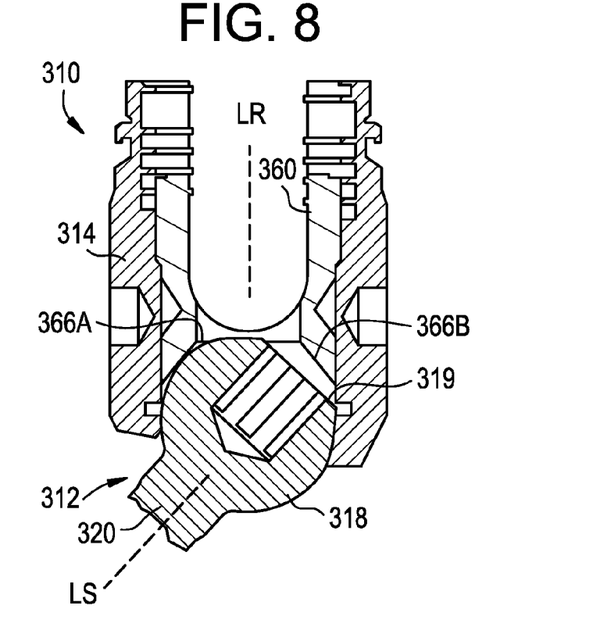
FIG. 8 is another sectional view of the bone anchor assembly of FIG. 6.

FIGS. 6-8 illustrate another exemplary embodiment of a bone anchor assembly 310 configured to provide feedback with regards to an orientation of the bone anchor 312 and/or to maintain a predetermined alignment between the bone anchor and the receiver member 314. As shown, the spherical head 318 of the bone anchor 312 is truncated along a proximal portion thereof to form a planar, proximal-facing surface 319 that can function as an orientation indication feature. For example, the planar surface 319 of the bone anchor 312 can cooperate with a distal-facing surface 366 of a compression member 360 to provide an indication as to the relative positioning of the shank 320 and the receiver member 314 (e.g., in the form of tactile or audible feedback). The planar surface 319 of the bone anchor 312 can also cooperate with the distal-facing surface 366 of the compression member 360 to selectively lock said relative positioning.

The distal-facing surface 366 can have a shape generally corresponding to the shape of a proximal portion of the head 318. Specifically, the distal-facing surface 366 can include a planar surface portion 366A that substantially corresponds in size and shape to the planar surface 319 of the bone anchor 312, and a spherical surface portion 336B that substantially corresponds in size and shape to a proximal, spherical portion of the head 318. In particular, the spherical surface portion 366B can have a radius of curvature similar or equal to a radius of curvature of the head 318.

FIG. 6 illustrates the bone anchor assembly 310 in an unlocked configuration before the compression member 360 has been tightened against the head 318. In this configuration, the bone anchor 312 can be freely angulated with respect to the receiver member 314 (subject to the normal constraints imposed by the geometry of the head 318 and the seat of the receiver member).

In FIG. 7, the bone anchor assembly 310 is shown in a first locked configuration in which the compression member 360 is advanced distally within the receiver member 314 and in which the planar surface 366A of the compression member is parallel to and engaged with the planar surface 319 of the head 318. In this position, flat-on-flat engagement provided between the planar surfaces 319, 366A firmly locks the bone anchor 312 at a fixed angle with respect to the receiver member 314. This can advantageously allow for high levels of torque to be applied to the receiver member 314 with minimal or zero slippage of the bone anchor 312 with respect to the receiver member, which can be useful in derotation maneuvers or other surgical manipulations. By transitioning the bone anchor assembly 310 to the first locked configuration, the polyaxial construct can essentially be converted to a monoaxial construct. In the illustrated embodiment, the first locked configuration fixes the construct in a coaxial position in which the longitudinal axis LS of the shank 320 is parallel to and collinear with the longitudinal axis LR of the receiver member 314. In other embodiments, the planar surface 319 of the head 318 can be oriented at an oblique angle with respect to the longitudinal axis LS and/or the planar surface 366A of the compression member 360 can be oriented at an oblique angle with respect to the longitudinal axis LR to provide rigid and robust locking in a non-coaxial position.

The compression member 360 can be advanced distally to position the assembly 310 in the first locked position in any of a variety of ways. For example, a set screw (e.g., the outer set screw shown in FIG. 1) can be threadably advanced within the receiver member 314 to urge the compression member 360 distally. By way of further example, an insertion instrument can be used to exert a distal force on the compression member 360. The insertion instrument can be threaded into the receiver member 314 to push the compression member distally 360, or can have an outer shaft that engages the receiver member and an inner shaft that can be slidably advanced with respect to the outer shaft to urge the compression member distally. As yet another example, the compression member 360 can be biased towards the first locked position, for example by selecting the geometry of the interface between the receiver member 314 and the compression member to create a spring biased relationship therebetween (e.g., based at least in part on the resiliency of the material from which the compression member is formed). As a still further example, a force can be applied to a spinal rod or other stabilization element disposed in the receiver member 314 to push the compression member 360 distally into the first locked position.

Partially or fully transitioning the bone anchor assembly 310 to the first locked configuration can generate tactile or audible feedback to a user, or resistance to angulation that is perceptible to a user (e.g., as the planar surfaces 319, 366A engage one another).

In FIG. 8, the bone anchor assembly 310 is shown in a second locked configuration in which the compression member 360 is advanced distally within the receiver member 314 and in which the planar surface 366A of the compression member is not parallel to and does not necessarily engage with the planar surface 319 of the head 318. Rather, the compression member 360 engages the spherical portion of the screw head 318. In this configuration, the assembly 310 can function in a conventional manner to lock the bone anchor 312 at any of a variety of angles with respect to the receiver member 314. While the relative positioning of the bone anchor 312 and the receiver member 314 is locked in the second locked configuration, it may not be locked as securely as when the assembly 310 is locked in the first locked configuration. In other words, in some embodiments, the second locked configuration can provide sufficient locking for long-term implantation of a spinal stabilization construct, but may not provide ideal or maximal locking for derotation and other maneuvers that require application of significant torque to the receiver member. The first locked configuration can be used in such instances to provide rigid and reliable locking.

In use, the bone anchor assembly 310 can be implanted in a patient (e.g., in a bone structure such as a pedicle or lateral mass of a vertebra) using standard techniques. After the assembly is implanted, or at any time during the implantation of the assembly, the user can assess the trajectory of the shank 320 by adjusting the angle of the receiver member 314 with respect thereto until the orientation indicating features of the head 318 and the receiver member 314 engage one another. Such engagement can produce audible or tactile feedback to the user, or a resistance to further relative movement that is perceptible to the user, to indicate that a predetermined relative positioning of the shank 320 and the receiver member 314 has been reached. The user can know which predetermined relative positioning (coaxial, maximum angulation, etc.) is indicated by the feedback, said knowledge being obtained, for example, by inspecting the assembly before insertion or by reviewing training or packaging materials associated with the assembly. In the illustrated embodiment, the user can know that receipt of such feedback means that the longitudinal axis of the shank 320 is aligned with the longitudinal axis of the receiver member 314. The user can therefore estimate the trajectory of the shank 320 in bone by observing the angle of the receiver member 314 with respect to the bone (visually or otherwise) and estimating or extrapolating from that angle the angle of the shank 320 with respect to the bone.

The user can also transition the assembly 310 between the unlocked configuration and the first or second locked configurations as desired. For example, the assembly 310 can be implanted initially in the unlocked configuration and then transitioned to the first locked configuration by compressing the compression member 360 against the head 318 of the bone anchor 312. Notably, the assembly 310 can be positioned in the first locked configuration without seating a spinal fixation element therein and/or without tightening a closure mechanism of the assembly 310. While in the first locked configuration, the user can exert a force on the receiver member to rotate or otherwise reposition a vertebra to which the assembly 310 is coupled. The user can then transition the assembly 310 to the unlocked configuration to allow an angle of the receiver member 314 relative to the shank 320 to be adjusted (e.g., to align the receiver member 314 with a spinal fixation element). The spinal fixation element can be positioned within the receiver member and the assembly can be transitioned to the second locked configuration (e.g., by tightening a set screw or other closure mechanism to force the spinal fixation element down onto the compression cap which is in turn compressed down onto the head of the bone anchor). The above-described method is merely exemplary, and can include fewer or additional steps and can be performed in any of a variety of sequences.

Figure 9:
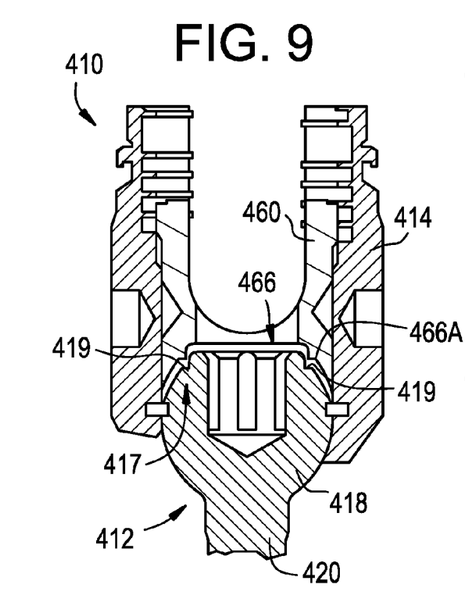
FIG. 9 is a sectional view of another embodiment of a bone anchor assembly having an orientation indication feature.
Figure 10:
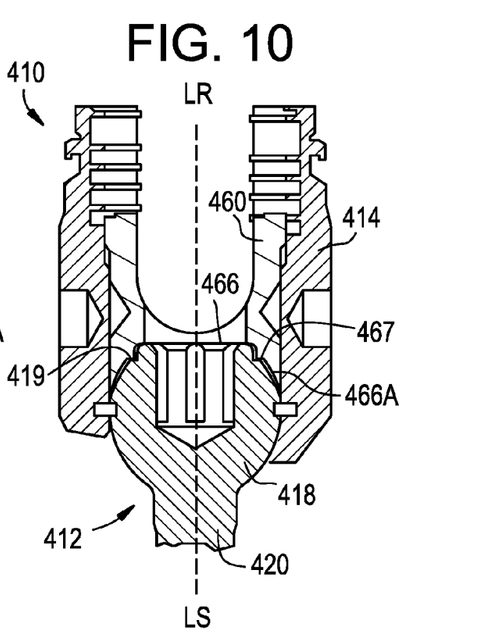
FIG. 10 is another sectional view of the bone anchor assembly of FIG. 9.
Figure 11:
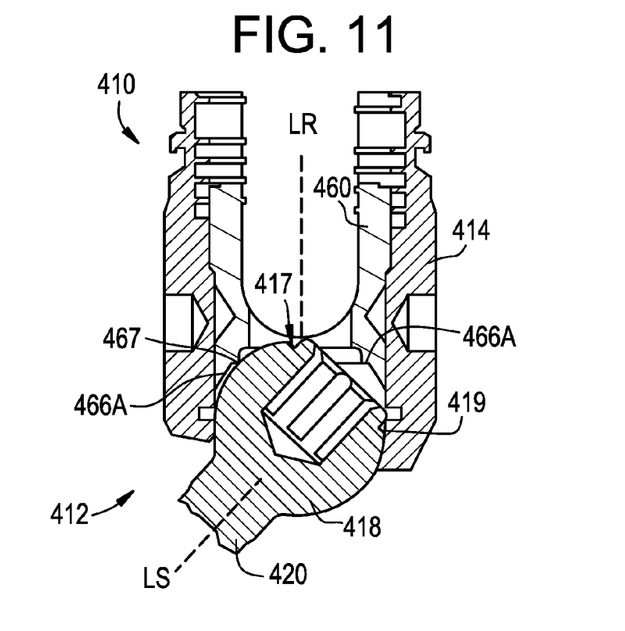
FIG. 11 is another sectional view of the bone anchor assembly of FIG. 9.

FIGS. 9-11 illustrate another exemplary embodiment of a bone anchor assembly 410 configured to provide feedback with regards to an orientation of the bone anchor 412 and/or to maintain a predetermined alignment between the bone anchor and the receiver member 414. The assembly 410 is generally similar to the assembly 310 described above, with one exception being the location of the planar surfaces.

As shown, the bone anchor 412 includes a groove 417 formed in an upper hemisphere of the head 418. The groove 417 is disposed distally to the proximal-most end of the head 418. At least a portion of the groove 417 defines a planar, proximal-facing surface 419 that can function as an orientation indication feature. For example, the planar surface 419 of the bone anchor 412 can cooperate with a distal-facing surface 466 of the compression member 460 provide an indication as to the relative positioning of the shank 420 and the receiver member 414 (e.g., in the form of tactile or audible feedback). The planar surface 419 of the bone anchor 412 can also cooperate with the distal-facing surface 466 of the compression member 460 to selectively lock said relative positioning.

The distal-facing surface 466 can have a shape generally corresponding to the shape of a proximal portion of the head 418. Specifically, the distal-facing surface 466 can be substantially spherical and can have a radius of curvature equal or approximately equal to that of the head 418. The distal-facing surface 466 can also include an annular ridge or protrusion 467, at least a portion of which defines a planar surface 466A that substantially corresponds in size and shape to the planar surface 419 of the bone anchor 412.

FIG. 9 illustrates the bone anchor assembly 410 in an unlocked configuration before the compression member 460 has been tightened against the head 418. In this configuration, the bone anchor 412 can be freely angulated with respect to the receiver member 414 (subject to the normal constraints imposed by the geometry of the head 418 and the seat of the receiver member).

In FIG. 10, the bone anchor assembly 410 is shown in a first locked configuration in which the compression member 460 is advanced distally within the receiver member 414 and in which the planar surface 466A of the compression member is parallel to and engaged with the planar surface 419 of the head 418. In this position, flat-on-flat engagement provided between the planar surfaces 419, 466A firmly locks the bone anchor 412 at a fixed angle with respect to the receiver member 414. This can advantageously allow for high levels of torque to be applied to the receiver member 414 with minimal or zero slippage of the bone anchor 412 with respect to the receiver member, which can be useful in derotation maneuvers or other surgical manipulations. By transitioning the bone anchor assembly 410 to the first locked configuration, the polyaxial construct can essentially be converted to a monoaxial construct. In the illustrated embodiment, the first locked configuration fixes the construct in a coaxial position in which the longitudinal axis LS of the shank 420 is parallel to and collinear with the longitudinal axis LR of the receiver member 414. In other embodiments, the planar surface 419 of the head 418 can be oriented at an oblique angle with respect to the longitudinal axis LS and/or the planar surface 466A of the compression member 460 can be oriented at an oblique angle with respect to the longitudinal axis LR to provide rigid and robust locking in a non-coaxial position.

The assembly 410 can advantageously have a reduced overall profile as compared with the assembly 310, since the positioning of the planar surfaces 419, 466A allows the compression member 460 to be disposed in a more-distal portion of the receiver member 414 when the assembly is in the first locked configuration.

The compression member 460 can be advanced distally to position the assembly 410 in the first locked position in any of the ways described above. Transitioning the bone anchor assembly 410 to the first locked configuration can generate tactile or audible feedback to a user, or resistance to angulation that is perceptible to a user (e.g., as the planar surfaces 419, 466A engage one another.

In FIG. 11, the bone anchor assembly 410 is shown in a second locked configuration in which the compression member 460 is advanced distally within the receiver member 414 and in which the planar surface 466A of the compression member is not parallel to and does not engage with the planar surface 419 of the head 418. Rather, the ridge 467 of the compression member 460 engages the spherical portion of the screw head 318. In this configuration, the assembly 410 can function in a conventional manner to lock the bone anchor 412 at any of a variety of angles with respect to the receiver member 414. While the relative positioning of the bone anchor 412 and the receiver member 414 is locked in the second locked configuration, it may not be locked as securely as when the assembly 410 is locked in the first locked configuration. In other words, in some embodiments, the second locked configuration can provide sufficient locking for long-term implantation of a spinal stabilization construct, but may not provide ideal or maximal locking for derotation and other maneuvers that require application of significant torque to the receiver member. The first locked configuration can be used in such instances to provide rigid and reliable locking.

The assembly 410 can be used in the same manner as the assembly 310 described above.

The above-described features for indicating an orientation of a bone anchor are not intended to be limiting. For example, any of the recesses and/or channels described herein can instead be formed as ridges and/or protrusions, and vice versa. Furthermore, either one or both of a bone anchor head and a compression member can have a plurality of surface features that function as orientation indication features. Using the embodiment of FIGS. 2-4 as an example, the compression member 160 can have a plurality of ridges, similar to the ridge 164, each of which can be configured to engage the recess 122 of the head 118 when the anchor 112 is oriented at a particular angle. The ridges can be of any size, shape, and number, and can extend in any plane and at regular or irregular intervals along the distal-facing surface 166 of the compression member 160. Such embodiments can thus provide the user with feedback for multiple orientations of the anchor 112. Similarly, the head 118 can have multiple recesses formed therein, similar to the recess 122, at regular intervals along the head 118. Each recess can engage the ridge 164 and/or the drag ring 150 to indicate that the anchor 112 has reached the next successive orientation.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A bone anchor assembly, comprising:
    a bone anchor having a proximal head and a distal shank; and
    a receiver member having a seat formed therein configured to movably seat the head of the bone anchor such that the shank of the bone anchor can be positioned at a plurality of angles with respect to the receiver member;
    wherein the head of the bone anchor includes an orientation indication feature that engages an orientation indication feature of the receiver member to provide feedback when the shank is positioned in a predetermined orientation with respect to the receiver member,
    wherein the indication feature of the head comprises a groove formed in the head, and wherein the indication feature of the receiver member comprises a drag ring configured to engage the groove when the shank is positioned in the predetermined orientation.

2. The assembly of claim 1, wherein the groove extends circumferentially around the head, perpendicular to a longitudinal axis of the bone anchor.

3. The assembly of claim 1, wherein the drag ring is seated within the groove only when the bone anchor is positioned at the predetermined orientation with respect to the receiver member.

4. The assembly of claim 1, wherein the indication feature of the receiver member comprises a groove formed in the seat of the receiver member and wherein the indication feature of the head comprises a drag ring configured to engage the groove when the shank is positioned in the predetermined orientation.

5. The assembly of claim 1, wherein the predetermined orientation is one in which the bone anchor is positioned at a maximum angle with respect to the receiver member.

6. The assembly of claim 1, wherein the head includes a plurality of orientation indication features, each of the plurality of orientation indication features being configured to engage an orientation indication feature of the receiver member to provide feedback when the shank is positioned in a corresponding one of a plurality of predetermined orientations with respect to the receiver member.

7. A bone anchor assembly, comprising:
    a bone anchor having a proximal head and a distal shank; and
    a receiver member having a seat formed therein configured to movably seat the head of the bone anchor such that the shank of the bone anchor can be positioned at a plurality of angles with respect to the receiver member;
    wherein the head of the bone anchor includes an orientation indication feature that engages an orientation indication feature of the receiver member to provide feedback when the shank is positioned in a predetermined orientation with respect to the receiver member, and
    wherein the indication feature of the head comprises first and second radial protrusions formed on the head and wherein the indication feature of the receiver member comprises a drag ring configured to sit between the first and second radial protrusions when the shank is positioned in the predetermined orientation.

8. The assembly of claim 7, wherein the first and second radial protrusions extend circumferentially around the head, perpendicular to a longitudinal axis of the bone anchor.

9. A bone anchor assembly, comprising:
a bone anchor having a proximal head and a distal shank; and
a receiver member having a seat formed therein configured to movably seat the head of the bone anchor such that the shank of the bone anchor can be positioned at a plurality of angles with respect to the receiver member;
wherein the head of the bone anchor includes an orientation indication feature that engages an orientation indication feature of the receiver member to provide feedback when the shank is positioned in a predetermined orientation with respect to the receiver member,
wherein the indication feature of the receiver member comprises first and second radial protrusions formed on the seat of the receiver member and wherein the indication feature of the head comprises a drag ring configured to sit between the first and second radial protrusions when the shank is positioned in the predetermined orientation.

10. A bone anchor assembly, comprising:
a bone anchor having a proximal head and a distal shank; and
a receiver member having a seat formed therein configured to movably seat the head of the bone anchor such that the shank of the bone anchor can be positioned at a plurality of angles with respect to the receiver member;
wherein the head of the bone anchor includes an orientation indication feature that engages an orientation indication feature of the receiver member to provide feedback when the shank is positioned in a predetermined orientation with respect to the receiver member, and
wherein the predetermined orientation is one in which a longitudinal axis of the bone anchor is parallel to a longitudinal axis of the receiver member.

11. A bone anchor assembly, comprising:
a bone anchor having a proximal head and a distal shank; and
a receiver member having a seat formed therein configured to movably seat the head of the bone anchor such that the shank of the bone anchor can be positioned at a plurality of angles with respect to the receiver member;
wherein the head of the bone anchor includes an orientation indication feature that engages an orientation indication feature of the receiver member to provide feedback when the shank is positioned in a predetermined orientation with respect to the receiver member, and
wherein the predetermined orientation is one in which the bone anchor is positioned normal to an obliquely-angled distal-facing surface of the receiver member.

12. A bone anchor assembly, comprising:
a bone anchor having a proximal head and a distal shank, the proximal head including a planar surface and a spherical surface;
a receiver member having a polyaxial seat formed in a distal end thereof and configured to polyaxially seat the head of the bone anchor; and
a compression member disposed within the receiver member and having a distal end that engages the proximal head of the bone anchor, the distal end including a planar surface;
wherein the assembly is positionable in a first locked configuration in which the planar surface of the head and the planar surface of the compression member are parallel to and engaged with one another to lock an orientation of the shank relative to the receiver member; and
wherein the planar surface of the head comprises a proximal-facing surface of a groove formed in the head at a location distal to a proximal-most end of the bone anchor.

13. The assembly of claim 12, wherein the assembly is positionable in a second locked configuration in which the planar surface of the head and the planar surface of the compression member are not parallel to one another and in which the compression member engages the head to lock an orientation of the shank relative to the receiver member.

14. The assembly of claim 12, wherein the planar surface of the compression member comprises a distal-facing surface of an annular ridge formed on the compression member.

15. The assembly of claim 12, wherein the assembly is biased towards the first locked configuration.

16. A surgical method, comprising:
advancing a distal shank of a bone anchor into a bone while a proximal head of the bone anchor is seated in a receiver member;
adjusting an angle of the receiver member with respect to the bone anchor until an orientation indication feature of the head engages an orientation indication feature of the receiver member to generate feedback indicative of a relative positioning between the bone anchor and the receiver member; and
determining a trajectory of the bone anchor in the bone based on the relative positioning indicated by said feedback.

17. The method of claim 16, further comprising positioning a planar surface of a compression member disposed in the receiver member with respect to a planar surface of the head such that the planar surfaces are parallel to and engaged with one another to lock a relative position between the bone anchor and the receiver member.

* * * * *